United States Patent [19]

Sowton

[11] 4,386,615

[45] Jun. 7, 1983

[54] ELECTRODES FOR CARDIAC PACEMAKERS

[76] Inventor: Edgar Sowton, 10 Beech Ave., Sanderstead, Surrey CR2 ONL, England

[21] Appl. No.: 175,346

[22] Filed: Aug. 4, 1980

[51] Int. Cl.³ .............................................. A61N 1/04
[52] U.S. Cl. ................................... 128/786; 178/419 P
[58] Field of Search ...................... 128/419 P, 784–786

[56] References Cited

U.S. PATENT DOCUMENTS

| | | | |
|---|---|---|---|
| 3,348,548 | 10/1967 | Chardack | 128/786 |
| 3,865,118 | 2/1975 | Bures | 128/786 |
| 3,949,757 | 4/1976 | Sabel | 128/786 |

*Primary Examiner*—William E. Kamm
*Attorney, Agent, or Firm*—Brooks, Haidt, Haffner & Delahunty

[57] ABSTRACT

A dual electrode for use in cardiac pacemaking to enable both ventricular and atrial electrical contact to be made. The electrode is formed as a catheter for passing through a blood vessel to the heart and has a ventricular electrode at its distal end. Spaced back from the distal end are one or more atrial electrodes (2) in a plane transverse to the catheter and spaced radially apart therefrom. The or each atrial electrode is supported in a material (14) sufficiently flexible and resilient to enable the atrial electrode(s) to distort out of the plane and pass through the blood vessel. The atrial electrodes may be formed as separate prongs, or a single continuous electrode may be formed (to resemble a small floppy disc). Means such as springs (12) may be provided to increase the resilience of the material (14) supporting the atrial electrodes (2).

9 Claims, 10 Drawing Figures

ELECTRODES FOR CARDIAC PACEMAKERS

This invention relates to electrodes for cardiac pacemakers, and particularly to transvenous electrodes suitable for atrial sensing and ventricular pacing, for A-V sequential pacing or bifocal pacing.

There are many occasions when it is desirable to control an artificial cardiac pacemaker by physiological methods, or to maintain physiological atrial-ventricular timing during pacing. Such instances include detection of activity from the sinus node or the atrium (right or left) using this activity to activate a cardiac pacemaker with subsequent delivery of a stimulus to the ventricle (right or left), or to another suitable pacing site. A delay may be incorporated between sensing the supraventricular impulse and delivery of the ventricular stimulating impulse.

Under other circumstances, it may be desirable to pace both the atrium and the ventricle, with or without any intervening delay.

Present techniques for reliable sensing of supraventricular impulses usually rely on attachment of a separate sensing electrode placed independently from the stimulating electrode. Dual electrodes for sensing the atrium and pacing the ventricle are so far unreliable. It is extremely difficult to pace the atrium or adjoining tissues, such as the sinus node, unless a separate electrode is attached so that A-V sequential pacing requires complicated electrode placement.

I have now developed a transvenous dual electrode suitable for the above applications and which can be reliably and simply placed in position.

According to the invention I provide a dual electrode for use in cardiac pacemaking to enable both ventricular and atrial electrical contact to be made, which comprises a catheter for insertion through a blood vessel to the heart and having at its distal end a ventricular electrode electrically-connected to the proximal end of the catheter, and, spaced apart from the ventricular electrode, at least one atrial electrode disposed in a plane transverse to the catheter and spaced radially apart therefrom, said at least one atrial electrode being supported in a material connected to said catheter which is sufficiently flexible and resilient to enable the atrial electrode(s) to be deformed out of said plane and pass through said blood vessel, said atrial electrode(s) being electrically-connected to the proximal end of the catheter.

The electrodes are preferably formed as prongs extending outwardly from the catheter. At least two, and preferably three such prongs are employed.

Preferred features of the present invention will now be described with reference to the accompanying drawing, given by way of example, wherein.

Figure 1:
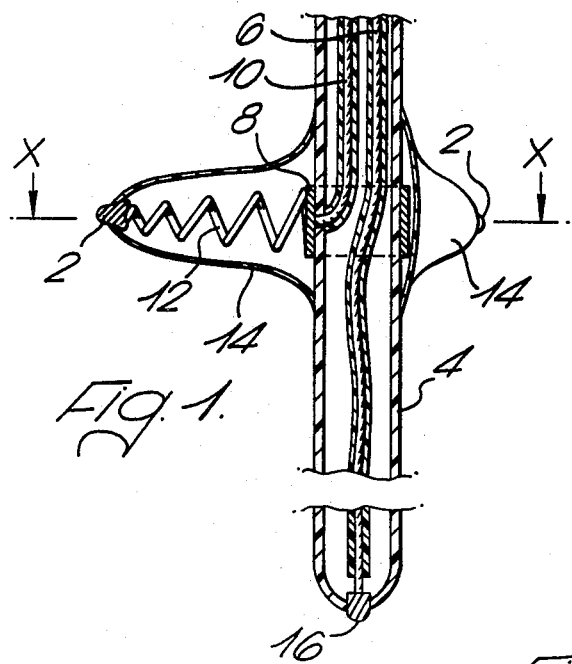
FIG. 1 is a cross-section through a dual electrode of the invention with the ventricular stimulating tip omitted.
Figure 2:
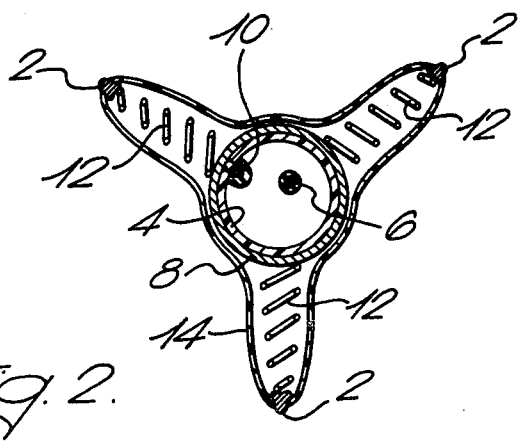
FIG. 2 is a section along the line X—X of FIG. 1.
Figure 3:
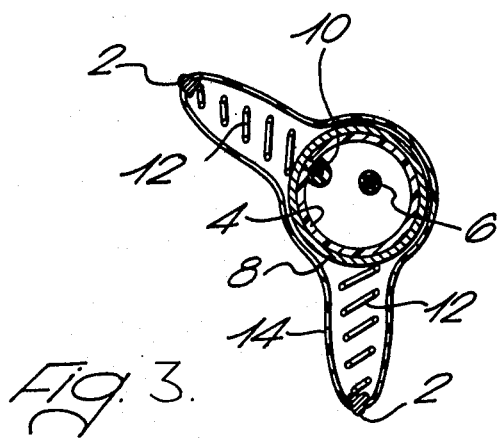
FIG. 3 is a section, similar to FIG. 2, of the dual electrode of the invention with two atrial electrodes.
Figure 4:
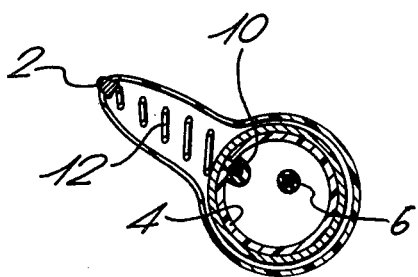
FIG. 4 is similar to FIG. 3 and illustrates one atrial electrode.

Referring to the drawing, the dual electrode illustrated has a ventricular stimulating tip electrode 16 at its distal end and three atrial electrodes 2. The ventricular tip electrode employed may be any of those currently in use, for example a screw-in or contact type, with a surface shape and area as desired. The atrial electrodes 2 are disposed approximately 13 to 17 cms back from the tip and are radially-disposed about a central catheter 4 of electrically-insulating flexible plastics tubing. An insulated electrical conductor 6 which makes connection with the ventricular tip electrode passes along catheter 4 to the proximal terminal of the electrode, as is conventional. Although three atrial electrodes are shown, it will be apparent that one or two of the electrodes 2 may be omitted. FIGS. 3 and 4 illustrate such embodiments.

An electrically-conductive metal ring 8 makes contact with and circumscribes catheter 4. Electrically connected to ring 8 and passing through the catheter wall is a second insulated electrical conductor 10. Also connected to ring 8 and extending radially outwardly therefrom are three electrically-conductive metal springs 12. The springs are respectively connected to an atrial electrode 2 and enable electrical connection between the atrial electrodes 2 and conductor 10 to be made. The conductor 10 passes along catheter 4 to the proximal terminal of the electrode.

The atrial electrodes 2 are maintained in a sheath of thin electrically-insulating flexible plastics material 14. The electrodes thus form three radially-disposed prongs biassed outwardly under the influence of springs 12. The radial length of each prong is typically from 0.5 to 1.5 cms. The sheath 14 is sealed to catheter 4 just beyond each side of the prongs.

The prongs are flexible and therefore allow the entire electrode to be introduced through a vein of suitable size such as the jugular subclavian or cephalic. The stimulating distal tip of the electrode can be positioned in the ideal position within the right ventricle and the prongs will then make contact with the lateral wall of the right atrium even although the course of the electrical conductors 6 and 10 lies within the cavity of the right atrium, away from the wall.

Figure 5:
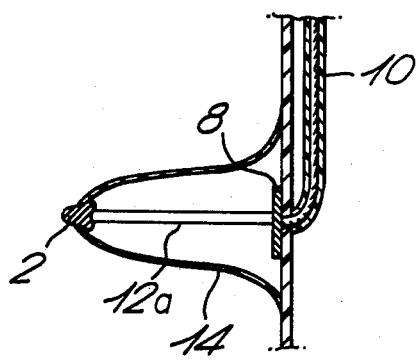
FIG. 5 is an axial section showing a flexible rod in place of the spring shown in FIG. 1.

The prongs are of such flexibility as to make adequate contact with the right atrial wall at one or more points and the tips are conductive with small area electrodes. The stiffness of the prongs can be influenced by the sheath material chosen (such as silicone rubber), by the dimensions and shape of the prongs, or by the incorporation of central stiffness such as the springs illustrated or flexible rod of metal 12a shown in FIG. 5.

The contact tips of the prongs can be shaped with a small radius of curvature to provide a high current density and pacing will occur through whichever of the prongs is contacting the atrial wall.

Figure 6:
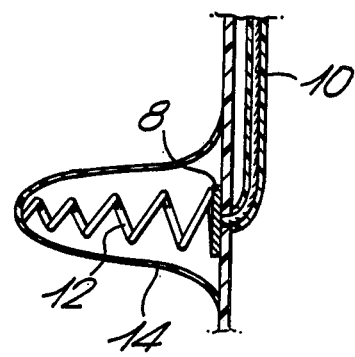
FIG. 6 is a section similar to FIG. 1 in which a "filled" atrial electrode replaces the electrode of FIG. 1.
Figure 7:
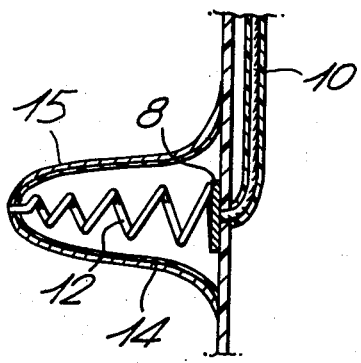
FIG. 7 is a section similar to FIG. 1 in which the electrode of FIG. 1 is replaced by a conductive coating on the sheath.

The prongs can alternatively be made conducting themselves, for example, by "filling" the insulating material 14 with biocompatible conducting elements such as carbon, as illustrated in FIG. 6 or by surface coating with a flexible conducting layer of biocompatible material, such as gold, as illustrated by 15 in FIG. 7.

Figure 8:
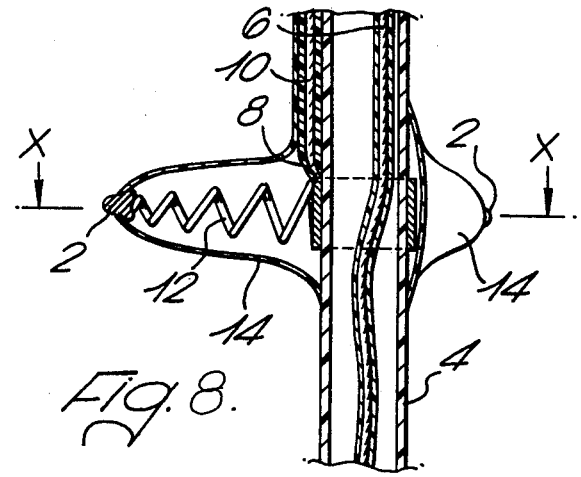
FIG. 8 is a section similar to FIG. 1 in which the sheath supporting the atrial electrode extends to the proximal end of the electrode and one of the conductors is outside the catheter.

Various modifications to the dual electrode described are possible. For example, the sheath 14 might only be sealed to the catheter 4 on the distal side of the prongs. On the proximal side the sheath 14 could then extend to the proximal end of the electrode with the conductor 10 extending to the proximal end in the annular gap between catheter 4 and sheath 14. In this manner, catheter 4 need not be pierced to allow passage of conductor 10 therethrough and, indeed, the insulation of one or both of conductors 6 and 10 could be omitted if desired. Such embodiment is illustrated in FIG. 8.

The invention is not restricted to the use of three atrial electrodes and more, or less prongs could be employed if wished, although 3, in the configuration illustrated, is thought to be the optimum.

Figure 9:
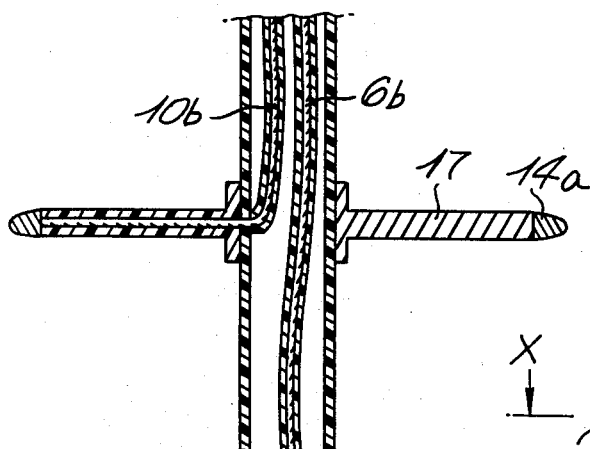
FIG. 9 is a section similar to FIG. 1 in which the separate electrodes are replaced by a floppy disc with a single, continuous electrode circumscribing the catheter.

In place of separate, radially-extending electrodes a single continuous atrial electrode, spaced apart from and circumscribing catheter 4, may be employed. In this embodiment, illustrated in FIG. 9 the atrial electrode would be similar to a small floppy disc extending outwardly from catheter 4.

Figure 10:
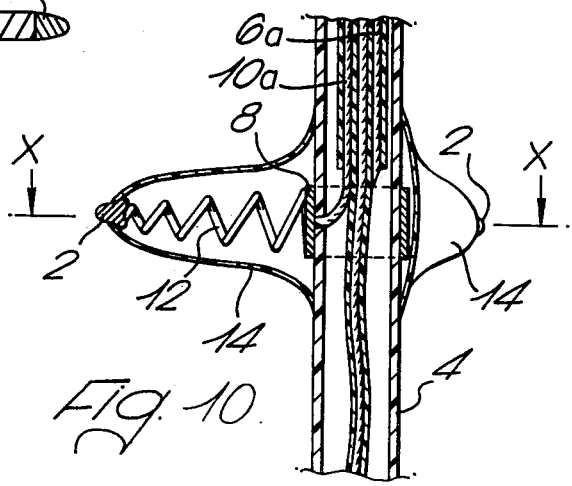
FIG. 10 is a section similar to FIG. 1 in which the conductors connected to the electrodes are co-axial.

Furthermore, in place of separate conductors for the atrial and ventricular electrodes, a coaxial cable with twin coaxial conductors may be employed, as illustrated in FIG. 10, the conductor 10a being co-axial with the conductor 6a.

I claim:

1. A dual electrode for use in cardiac pacemaking and which simultaneously provides both ventricular and atrial electrical contact, said electrode comprising:
   a relatively long and narrow catheter for insertion into the heart through a blood vessel leading to the heart, said catheter having a longitudinal axis;
   a ventricular electrode for ventricular electrical contact disposed on the distal end of said catheter in an axially fixed position relative to the axis of said catheter;
   flexible and resilient mounting means extending radially outwardly from said catheter and perpendicular to the axis of the catheter and being secured to said catheter at its end nearest said catheter in a fixed axial position relative to the axis of said catheter, said mounting means carrying an atrial electrode at a position thereon spaced from said catheter and said mounting means normally maintaining said atrial electrode in a predetermined position radially outwardly of said catheter but permitting said atrial electrode to move from said position thereof toward said catheter with the application of forces thereto by said blood vessel as the catheter is moved through said blood vessel; and
   conductive means electrically connected to and extending from said ventricular electrode and said atrial electrode respectively to adjacent the proximal end of said catheter for making electrical connections to said ventricular electrode and to said atrial electrode.

2. A dual electrode according to claim 1 wherein said mounting means is a sheath of plastics material.

3. A dual electrode for use in cardiac pacemaking and which simultaneously provides both ventricular and atrial electrical contact, said electrode comprising:
   a relatively long and narrow catheter for insertion into the heart through a blood vessel leading to the heart, said catheter having a longitudinal axis;
   a ventricular electrode for ventricular electrical contact disposed on the distal end of said catheter in an axially fixed position relative to the axis of said catheter;
   flexible and resilient mounting means in the form of a sheath of plastics material extending radially outwardly from said catheter and being secured to said catheter at its end nearest said catheter in a fixed axial position relative to the axis of said catheter, said sheath being hollow and having the shape of a surface of revolution having a base at its end nearest said catheter which is greater than its end remote from said catheter and said sheath carrying an atrial electrode at the end of said sheath remote from said catheter, said mounting means normally maintaining said atrial electrode in a predetermined position radially outwardly of said catheter but permitting said atrial electrode to move from said position thereof toward said catheter with the application of forces thereto by said blood vessel as the catheter is moved through said blood vessel; and
   conductive means electrically connected to and extending from said ventricular electrode and said atrial electrode respectively to adjacent the proximal end of said catheter for making electrical connections to said ventricular electrode and to said atrial electrode.

4. A dual electrode according to claims 2 or 3 further comprising means within said sheath engaging said catheter at one end and engaging said sheath at its opposite end for opposing movement of said sheath and thereby increasing the resiliency thereof.

5. A dual electrode according to claims 2 or 3 wherein there are at least two said atrial electrodes mounted on said catheter, said two atrial electrodes being spaced from each other circumferentially of said axis.

6. A dual electrode according to claims 2 or 3 wherein there are three said atrial electrodes mounted on said catheter, said three atrial electrodes being equally spaced circumferentially of said axis.

7. A dual electrode for use in cardiac pacemaking and which simultaneously provides both ventricular and atrial electrical contact, said electrode comprising:
   a relatively long and narrow catheter for insertion into the heart through a blood vessel leading to the heart, said catheter having a longitudinal axis;
   a ventricular electrode for ventricular electrical contact disposed on the distal end of said catheter in an axially fixed position relative to the axis of said catheter;
   flexible and resilient mounting means extending radially outwardly from said catheter and being secured to said catheter at its end nearest said catheter in a fixed axial position relative to the axis of said catheter, said mounting means carrying an atrial electrode at a position thereon spaced from said catheter, said atrial electrode extending circumferentially of said axis and surrounding said catheter, and said mounting means normally maintaining said atrial electrode in a predetermined position radially outwardly of said catheter but permitting said atrial electrode to move from said position thereof toward said catheter with the application of forces thereto by said blood vessel as the catheter is moved through said blood vessel; and conductive means electrically connected to and extending from said ventricular electrode and said atrial electrode respectively to adjacent the proximal end of said catheter for making electrical connections to said ventricular electrode and to said atrial electrode.

8. A dual electrode for use in cardiac pacemaking and which simultaneously provides both ventricular and atrial electrical contact, said electrode comprising:
  a relatively long and narrow catheter for insertion into the heart through a blood vessel leading to the heart, said catheter having a longitudinal axis;
  a ventricular electrode for ventricular electrical contact disposed on the distal end of said catheter in an axially fixed position relative to the axis of said catheter;
  flexible and resilient mounting means extending radially outwardly from said catheter and being secured to said catheter at its end nearest said catheter in a fixed axial position relative to the axis of said catheter, said mounting means carrying said atrial electrode at a position thereon spaced from said catheter and said mounting means normally maintaining said atrial electrode in a predetermined position radially outwardly of said catheter but permitting said atrial electrode to move from said position thereof toward said catheter with the application of forces thereto by said blood vessel as the catheter is moved through said blood vessel; and conductive means electrically connected to and extending from said ventricular electrode and said atrial electrode respectively to adjacent the proximal end of said catheter for making electrical connections to said ventricular electrode and to said atrial electrode, the portion of said conductive means connected to said atrial electrode comprising a conductive ring surrounding and in contact with said catheter and conductive means interconnecting said ring and said atrial electrode.

9. A dual electrode according to claim 8 wherein said conductive means interconnecting said ring and said atrial electrode is a metal spring.

* * * * *

UNITED STATES PATENT AND TRADEMARK OFFICE
CERTIFICATE OF CORRECTION

PATENT NO. : 4,386,615

DATED : June 7, 1983

INVENTOR(S) : Edgar Sowton

It is certified that error appears in the above-identified patent and that said Letters Patent is hereby corrected as shown below:

Title page, after the line indicated as (22), insert:

--(30) Foreign Application Priority Data
August 28, 1979 (GB) United Kingdom ... 79/29735--

Column 1, line 58, delete "and".

Signed and Sealed this

Seventh Day of February 1984

[SEAL]

Attest:

GERALD J. MOSSINGHOFF

Attesting Officer

Commissioner of Patents and Trademarks